United States Patent [19]

Bernath et al.

[11] Patent Number: 4,654,351
[45] Date of Patent: Mar. 31, 1987

[54] BIS(SUBSTITUTED METHYL)-METHYL-ISOQUINOLINE DERIVATIVES AND PHARMACEUTICAL COMPOSITIONS CONTAINING THEM

[75] Inventors: Gabor Bernath; Jenő Kobor; Ferenc Fulop; Gabor Motika, all of Szeged; Attila Sohajda, Kisvarda; Elemer Ezer, Budapest; György Hajos, Budapest; Eva Palosi, Budapest; Laszlo Denes, Budapest; Laszlo Szporny, Budapest, all of Hungary

[73] Assignee: Richter Gedeon Vegyeszeti Gyar R.T., Budapest, Hungary

[21] Appl. No.: 664,849

[22] Filed: Oct. 25, 1984

[30] Foreign Application Priority Data

Oct. 25, 1983 [HU] Hungary ............................... 3653/83

[51] Int. Cl.[4] ..................... A61K 31/47; C07D 217/16
[52] U.S. Cl. .................................. 514/307; 546/146; 546/147; 546/149; 546/150
[58] Field of Search ................................ 546/146–147, 546/149–150; 514/307

[56] References Cited

U.S. PATENT DOCUMENTS

3,562,280  2/1971  Leimgruber et al. ............... 546/146
4,373,104  2/1983  Takács et al. ....................... 546/147

OTHER PUBLICATIONS

Chem. Ber. 102, 915 (1969).
G. Bernath, K. Kovács, K. L. Láng: Acta Chim. Sci. Hung. 65, 347 (1970).
Swinyard et al.: J. Pharmacol. Exp. Ther. 106, 319 (1952).
Niemegeers, C. J. E., et al.: Arzneimittel Forsch. 25:15/9 (1975).

*Primary Examiner*—Glennon H. Hollrah
*Assistant Examiner*—James H. Turnipseed
*Attorney, Agent, or Firm*—Keil & Weinkauf

[57] ABSTRACT

The invention relates to new bis(substituted methyl)-methyl-isoquinoline derivatives of the formula (I)

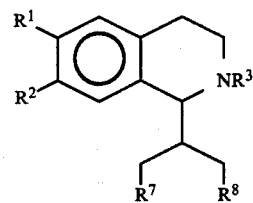

wherein
R[1] and R[2] represent hydroxyl or alkoxy having from 1 to 6 carbon atoms,
R[3] is hydrogen, aralkyl having from 1 to 4 carbon atoms in the alkyl moiety or a

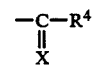

group, in which
R[4] is alkyl having from 1 to 5 carbon atoms, phenyl, substituted phenyl or —NH—phenyl,
X is oxygen or sulfur,
R[7] is hydroxyl, halogen or an

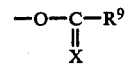

group,
R[8] is halogen, alkoxy from 1 to 4 carbon atoms or an

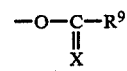

group, in which
X has the same meaning as defined above, and
R[9] independently from R[4] may have the same meanings as defined for R[4], or is an —NH(C[1-4]-alkyl) or C[3-6]-cycloalkyl group, and salts thereof. According to another aspect of the invention there are provided processes for the preparation of these compounds and pharmaceutical compositions containing them.

6 Claims, No Drawings

BIS(SUBSTITUTED METHYL)-METHYL-ISOQUINOLINE DERIVATIVES AND PHARMACEUTICAL COMPOSITIONS CONTAINING THEM

The invention relates to new bis(substituted methyl)-methyl-isoquinoline derivatives of the formula (I)

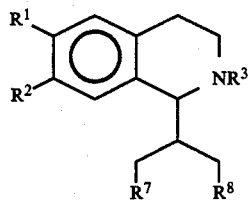  (I)

wherein
$R^1$ and $R^2$ represent hydroxyl or alkoxy having from 1 to 6 carbon atoms,
$R^3$ is hydrogen, aralkyl having from 1 to 4 carbon atoms in the alkyl moiety or a

group, in which
$R^4$ is alkyl having from 1 to 5 carbon atoms, phenyl, substituted phenyl or —NH-phenyl,
X is oxygen or sulfur,
$R^7$ is hydroxyl, halogen or an

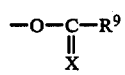

group,
$R^8$ is halogen, alkoxy having from 1 to 4 carbon atoms or an

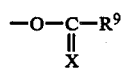

group, in which
X has the same meaning as defined above, and
$R^9$ independently from $R^4$ may have the same meanings as defined for $R^4$, or is an —NH($C_{1-4}$-alkyl) or $C_{3-6}$-cycloalkyl group, and salts thereof.

According to another aspect of the invention there is provided a process for the preparation of compounds of the formula (I) and salts thereof.

Compounds of the formula (I), in which $R^7$ and $R^8$ each represents halogen, $R^1$, $R^2$ and $R^3$ are as defined above, may be prepared by halogenating the corresponding compounds of the formula (II),

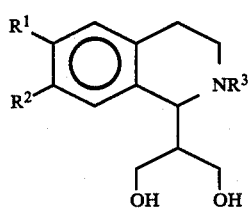  (II)

in which $R^1$, $R^2$ and $R^3$ are as defined above (process $a_1$). If desired, the compounds obtained may be alkoxylated at place of $R^8$ in a manner known per se.

Compounds of the formula (I), in which $R^7$ and $R^8$ each stands for a

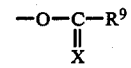

group, wherein X and $R^9$ are as hereinbefore defined, $R^1$, $R^2$ and $R^3$ are as defined above, are prepared according to the invention by reacting a compound of the formula (II), in which $R^1$, $R^2$ and $R^3$ are as defined above, with an acylating agent suitable for incorporating the

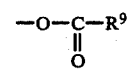

acyl group (process $a_2$).

According to another process compounds of formula (I) are prepared by converting an N-substituted bis(hydroxymethyl)-methyl-derivative of the formula (III)

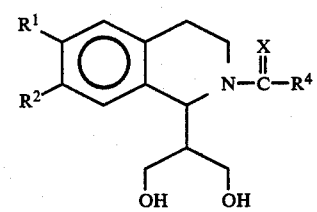  (III)

into a corresponding O-acyl derivative by N→O acyl migration ($R^1$, $R^2$, $R^4$ and X are as defined above), in the presence of a catalytic amount of an acid and, if desired, halogenating a compound of the formula (IV)

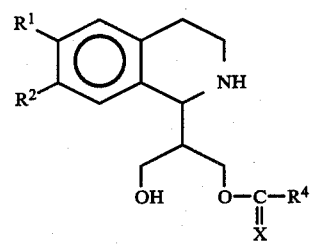  (IV)

obtained ($R^1$, $R^2$, $R^4$ and X are as defined above) or an acid addition salt thereof and, if desired, splitting off the acyl or thioacyl group from a compound of the formula (V)

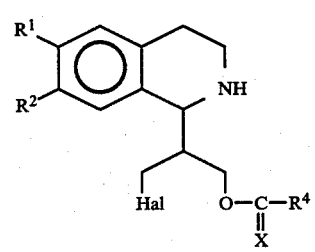  (V)

obtained ($R^1$, $R^2$, $R^4$ and X are as defined above, Hal is halogen) or, if desired, converting a compound of the formula (V) obtained into a corresponding compound of the formula (I), in which $R^3$ represents an

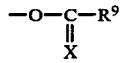

group ($R^4$ and X are as defined above), by O→N acyl migration, in an alkaline medium.

If desired, the substituents $R^1$ and/or $R^2$ and/or $R^3$ and/or $R^7$ and/or $R^8$ in the compounds of the formula (I) can be converted into other groups within the definition of the respective substituents by methods known per se, or compounds of formula (I) can be converted into their acid addition salts.

Compounds of the formula (I) are biologically active, thus show immunsuppressive, antidepressive, analgesic, antipyretic, antihypoxial or gastric acid secretion inhibiting activity. They are further useful intermediates in the preparation of biologically active 2H-azeto[2,1-a]-isoquinoline derivatives, which are disclosed in our co-pending Hungarian patent application No. 3655/83 which corresponds to U.S. application Ser. No. 664,786 filed Oct. 25, 1984. The latter compounds may, for example, be prepared by the ring closure of compounds of the formula (I), in which at least one of $R^7$ and $R^8$ stands for halogen, or a salt thereof.

According to Chem. Ber. 102, 915 (1969) 1-[bis(hydroxy-methyl)-methyl]-isoquinoline was prepared from 1-methyl-isoquinoline with formaldehyde. The compound was afforded in a yield of 60%, after boiling for 40 hours. The only reaction of the compound obtained examined in this article was its hydrogenation in the presence of platinum oxide catalyst, which resulted in the corresponding 5,6,7,8-tetrahydroisoquinoline in a 30% yield. No N-and/or O-substituted derivatives of these compounds were prepared, and it was neither disclosed nor suggested that the compounds or their derivatives would be pharmaceutically active.

In the above formulae, in the definition of $R^1$, $R^2$ and $R^8$ the term "alkoxy" is used to refer to straight or branched chained alkoxy groups, e.g. methoxy, ethoxy, n- or isopropoxy, n-, sec.- or tert.-butoxy, n- or isopentoxy, n- or isohexyloxy groups, depending on the limitation given for the number of carbon atoms. The preferred alkoxy groups contain 1 to 4 carbon atoms, more preferably they are methoxy or ethoxy.

The term "alkyl" as such or as part of other groups is used to refer to straight-chained or branched alkyl groups, such as e.g. methyl, ethyl, n-propyl, isopropyl, n-butyl, isobutyl, sec.-butyl, tert.-butyl, n-pentyl, isopentyl, n-hexyl and isohexyl groups, taking into account the limitations for the number of carbon atoms.

The term "aralkyl containing from 1 to 4 carbon atoms in the alkyl moiety" in the definition of $R^3$ preferably represents a $C_{1-4}$-alkyl-phenyl group, more preferably benzyl.

In the definition of $R^4$ and $R^9$ "phenyl" may be substituted by one or more substituents, preferably selected from the group consisting of halogen, alkyl having from 1 to 4 carbon atoms, alkoxy having from 1 to 4 carbon atoms and nitro. The term "halogen" is used to include all halogen atoms, i.e. fluorine, chlorine, bromine and iodine, preferably chlorine, bromine and iodine, more preferably chlorine.

X preferably stands for oxygen.

Compounds of the formula (I), in which $R^7$ is hydroxyl, $R^8$ is an

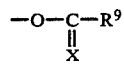

group (the other substituents are as defined above) are particularly preferred.

The isoquinoline derivatives of the formula (II), which are used as starting compounds in processes ($a_1$) and ($a_2$) according to the invention, are new compounds, the preparation of which is disclosed in our co-pending Hungarian patent applications Nos. 3651/83 and 3652/83 which correspond respectively to U.S. applications Ser. Nos. 664,842, filed Oct. 25, 1984, and 664,770 filed Oct. 25, 1984. compounds of the formula (II), in which $R^3$ stands for a hydrogen atom, may be prepared by reacting the corresponding 1-methyl-3,4-dihydroisoquinoline derivatives or the corresponding 1-($\beta$-hydroxyethyl)-3,4-dihydroisoquinoline derivatives with formaldehyde or the hydrate or trimeric derivatives thereof, in an alkaline medium, and subsequently hydrogenating the product obtained. The compounds in which $R^3$ is other than hydrogen may be prepared from the N-unsubstituted compounds by reactants suitable for the introduction of the desired $R^3$ groups, e.g. alkylation, aralkylation, acylation, etc. The 1-methyl- and 1-($\beta$-hydroxyethyl)-3,4-dihydroisoquinoline derivatives used for the preparation of the starting compounds of formula (II) are known in the art and can, for example, be prepared from homoveratryl amine or the corresponding phenylethyl amine derivatives by acylation and conventional isoquinoline cyclization reactions, e.g. Bischler-Napieralski synthesis.

The N-substituted bis(hydroxymethyl)-methyl isoquinoline derivatives of the formula (III) (process b)) are a sub-group of the compounds of formula (II), and can be prepared following the methods used for the preparation of the latter compounds, starting from the corresponding N-unsubstituted compounds.

Accordng to process ($a_1$) the compounds of the formula (I), in which $R^7$ and $R^8$ both stand for a halogen, are prepared by halogenating bis(hydroxymethyl)-methyl isoquinoline derivatives of the formula (II) ($R^1$, $R^2$ and $R^3$ are as hereinbefore defined). The halogenation can be performed with any conventional halogenating agent, under usual conditions of halogenation. Chlorination may be carried out with chlorine gas, but the reaction is easier to control if for example sulfinyl dichloride is used as a halogenating agent. Similarly, bromination may be performed with elementary bromine, but it is more preferred to use e.g. phosphorus tribromide as a brominating agent. The reaction conditions are selected depending on the concrete reactants employed.

According to process ($a_2$) compounds of the formula (I), in which $R^7$ and $R^8$ both represent an

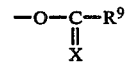

group, are prepared by reacting a corresponding compound of the formula (II) with a reactant suitable for introducing an acyl group of the above formula. Depending on the meaning of $R^9$, acylation may be performed with an acid halide, acid anhydride or—if $R^9$ is an —NH—$C_{1-4}$-alkyl or —NH-phenyl group—with a corresponding isocyanate or isothiocyanate, under reaction conditions conventional for acylation reactions.

The N-substituted bis(hydroxymethyl)-methyl derivatives of the formula (III) ($R^1$, $R^2$, $R^4$ and X are as defined above) can be converted into the corresponding O-acyl derivatives by N→O acyl migration, with acid catalysis, N→O acyl migration is a reversible chemical reaction well known in the organic chemistry, which proceeds into O→N direction under alkaline conditions [G. Bernáth, K. Kovács, K. L. Láng: Acta Chim. Sci. Hung. 65, 347 (1970)].

If desired, from the compounds, in which $R^7$ and/or $R^8$ is acyl, the acyl group(s) can be split off, for example by acid treatment, to yield compounds containing hydroxyl group(s) in the respective position(s). If desired, the acyl group(s) can be replaced by other acyl group(s) as well.

Compounds of the formula (I) can be converted into their acid addition salts by reaction with suitable acids.

Salt formation can be carried out, for example, in an inert organic solvent, such as a $C_{1-6}$ aliphatic alcohol, by dissolving the compound of the formula (I) in the solvent and adding the selected acid or a solution thereof formed with the same solvent to the first solution until it becomes slightly acidic (pH 5 to 6). Thereafter the acid addition salt separates and can be removed from the reaction mixture e.g. by filtration.

The compounds of the formula (I) or the salts thereof, if desired, can be subjected to further purification, e.g. recrystallization. The solvents used for recyrystallization are selected depending on the solubility and crystallization properties of the compound to be crystallized.

The new compounds of the formula (I) and their physiologically acceptable salts may be formulated for therapeutic purposes. The invention therefore relates also to pharmaceutical compositions comprising as active ingredient at least one compound of formula (I) or a physiologically acceptable salt thereof, in association with pharmaceutical carriers and/or excipients. Carriers conventional for this purpose and suitable for parenteral or enteral administration as well as other additives may be used. As carriers solid or liquid compounds, for example water, gelatine, lactose, milk sugar, starch, pectin, magnesium stearate, stearic acid, talc, vegetable oils, such as peanut oil, olive oil, arabic gum, polyalkylene glycols, and vaseline (registered Trade Mark), can be used. The compounds can be formulated as conventional pharmaceutical formulations, for example in a solid (globular and angular pills, dragées, capsules, e.g. hard gelatine capsules) or liquid (injectable oily or aqueous solutions or suspensions) form. The quantity of the solid carrier can be varied within wide ranges, but preferably is between 25 mg and 1 g. The compositions optionally contain also conventional pharmaceutical additives, such as preserving agents, wetting agents, salts for adjusting the osmotic pressure, buffers, flavouring and aroma substances.

The compositions according to the invention optionally contain the compounds of formula (I) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatment, such as sterilization.

For the pharmacological tests CFLP (LATI) mice of both sexes, weighing 18 to 22 g each and male Han. Wistar (LATI) rats weighing 160 to 180 g each were used. The test materials were administered orally, in 30 mg/kg doses, in the form of a suspension containing 5% of Tween 80, one hour before the tests.

TEST METHODS

1. Maximum electroshock (mice)

The shock was applied through a corneal electrode (20 mA, 0.2 msec, HSE Schockgerät typ. 207). The animals which do not show a tonic, extensoric spasm as a result of electroshock treatment are considered protected (See Swinyard et al.: J. Pharmacol. Exp. Ther. 106, 319 (1952)).

2. Metrazole spasm (mice)

After pretreatment, the animals were administered 125 mg/kg of pentylenetetrazole subcutaneously. The animals which did not show (a) a clonic, (b) a tonic extensoric spasm and which survived the experiment were regarded protected.

Observation time: one hour (Everett L. M. and Richards R. K.: J. Pharmacol. Exp. Ther. 81, 402 /1944/).

3. Inhibition of tetrabenazine catalepsy

The test was carried out on male rats each weighing 160 to 180 g. The test materials were administered intraperitoneally, in a dose of 30 mg/kg, one hour before tetrabenazine administration. The animals, which if their forlegs were placed on a 7 cm high pillar, did not correct their bizarre position within 30 seconds were regarded cataleptic (Delay J. and Denicker P.: Compt. Rend. Congr. Med. Alenistens Neurologists 19, 497 /Luxemb./).

4. Analgesic activity (mice)

One hour after pretreatment, mice were administered 0.4 ml of a 0.6% acetic acid solution intraperitoneally, as a pain stimulus. The frequency of writhing syndrom is registered for 30 minutes. The changes observed as a result of treatment with the test compounds are related to the mean value of the frequency of writhing syndrom in the control group, and the difference is expressed in percentage (Koster R. et al.: Exp. Ther. 72:74 /1941/).

5. Antipyretic activity (rats)

Hyperthermia is induced in rats with Brewer's yeast suspension (0.5% of Brewer's yeast, 1% of arabic gum in a volume of 0.3 ml, s.c.). The animals are treated with the test materials 4 hours later, and the tracheal temperature of the animals is registered with an ELAB thermometer (typ. TE-3) for 4 hours. The antipyretic activity is expressed in percentage of the animals which have an at least one centrigrade lower temperature than the average of the control group treated with the solvent (Nimegeers C. J. E. et al.: Arzneimittel Forsch. 25:15/9 /1975/).

The analgesic activity of 1-[1'-(hydroxymethyl)-1'-(benzoyl-oxymethyl)-methyl]-6,7-dimethoxy-1,2,3,4-tetrahydroisoquinoline hydrochloride (compound A) and 1-[1'-(hydroxymethyl)-1'-(m,p,m'-trimethoxybenzoyloximethyl)-methyl]-6,7-diethoxy-1,2,3,4-tetrahydroisoquinoline hydrochloride (compound B) is 4-times and 3.7-times, respectively, higher than that of Na-salycilate. The test results are set forth in Table 1.

TABLE 1

| Substances | Antispasm activity | | | Antitetra-benazine activity (%) | Analgesic activity (%) | Antipyretic activity (%) |
|---|---|---|---|---|---|---|
| | max. electro-shock | metrazole | | | | |
| | | a | b | | | |
| Compound A | 20.0 | — | 20.0 | 35.0$^x$ | 28.0$^x$ | 10.0 |
| Compound B | — | — | 20.0 | — | 30.0$^x$ | 30.0 |
| Na—salycilate | — | — | 20.0 | — | 113.0$^x$ | 110.0$^x$ |

The invention is elucidated in detail by the aid of the following non-limiting Examples.

EXAMPLE 1

Preparation of 1-[bis(chlormethyl)-methyl]-2-benzoyl-6,7-dimethoxy-1,2,3,4-tetrahydroisoquinoline (A) 1-[bis(Hydroxymethyl)-methyl]-2-benzoyl-6,7-dimethoxy-1,2,3,4-tetrahydroisoquinoline 0.01 mole (2.7 g) of 1-[bis(hydroxymethyl)-methyl]-6,7-dimethoxy-1,2,3,4-tetrahydroisoquinoline is dissolved in 50 ml of benzene with slight warming, and a solution of 0.015 mole (0.6 g) of sodium hydroxide in 10 ml of water is added to the solution. 0.011 mole (0.5 g) of benzoyl chloride is added dropwise to the reaction mixture, under cooling and stirring. When the addition of acid chloride is complete, the mixture is stirred at room temperature for one hour, whereupon the organic phase is separated, and the aqueous phase is extracted twice with chloroform. The combined organic phases are dried and evaporated to yield the aimed compound.

Melting point: 161° to 163° C. (methanol/ether). Yield: 95%. Analysis for $C_{21}H_{25}NO_5$ (371.43): calculated: C 67.91%, H 6.78%, N 3.77%; found: C 67.72%, H 6.98%, N 4.00%.

(B) To 0.01 mole (3.7 g) of 1-[bis(hydroxymethyl)-methyl]-2-benzoyl-6,7-dimethoxy-1,2,3,4-tetrahydroisoquinoline prepared according to Step (A)

0.04 mole (5 ml) of sulfinyl dichloride is added under ice cooling, in about 5 to 10 minutes. The reaction mixture is allowed to stand at room temperature for 24 hours, whereupon the excess of sulfinyl chloride is evaporated, the residue is cooled, alkalized with sodium bicarbonate solution, and extracted with three 30-ml portions of ether. The extract is dried over sodium sulfate and evaporated to about 10 ml. Upon cooling the aimed compound is obtained in a crystalline form.

Melting point: 170° to 171° C. (ethanol). Yield: 53%. Analysis for $C_{21}H_{23}Cl_2NO_3$ (408.31): calculated: C 61.77%, H 5.68%, N 3.43%, Cl 17.39%; found: C 61.35%, H 5,95%, N 3.80%, Cl 17.76%.

EXAMPLE 2

Preparation of 1-[1'-(hydroxymethyl)-1''-(benzoyloxymethyl)-methyl]-6,7-dimethoxy-1,2,3,4-tetrahydroisoquinoline hydrochloride 0.01 mole (3.7 g) of 1-[bis(hydroxymethyl)-methyl]-2-benzoyl-6,7-dimethoxy-1,2,3,4-tetrahydroisoquinoline prepared according to Step A of Example 1 is dissolved in 20 ml of absolute ethanol. An excess amount of an absolute ethanolic hydrogen chloride solution is added to the solution and the reaction mixture is then refluxed for 4 hours. Thereafter the reaction mixture is evaporated, and the obtained crystalline product is recrystalized from absolute ethanol.

Melting point: 211° to 214° C. Yield: 95%. Analysis for $C_{21}H_{26}ClNO_5$ (407.90): calculated: C 61.84%, H 6.42%, N 3.43%; found: C 61.78%, H 6.55%, N 3.60%.

The compounds set forth in Table 1 can be prepared in an analogous manner, by proper selection of the starting substances. The reflux time, depending on the substituent of the acyl group, is between one and six hours.

TABLE 1

1-[1'-(Hydroxymethyl)-1'-(O—acyl)-methyl]-6,7-dialkoxyl-1,2,3,4-tetrahydroisoquinoline hydrochlorides of formula (I/1)

| Example | $R^1 = R^2$ | $R^9$ | Formula/ Molecular weight | Melting point (°C.) Solvent | | Analysis calculated | found | Yield (%) |
|---|---|---|---|---|---|---|---|---|
| 3 | $CH_3O$ | $CH_3$ | $C_{16}H_{24}ClNO_5$ 345.82 | 208–210 ethanol | C: H: N: | 55.57 7.00 4.05 | 55.97 7.37 4.20 | 93 |
| 4 | $C_2H_5O$ | $CH_3$ | $C_{18}H_{28}ClNO_5$ 373.86 | 193–197 ethanol | C: H: N: | 57.82 7.55 3.75 | 58.07 7.92 3.54 | 91 |
| 5 | $C_2H_5O$ | $C_6H_5$ | $C_{23}H_{30}ClNO_5$ 435.95 | 182–184 ethanol/ether | C: H: N: | 63.37 6.94 3.21 | 62.96 7.20 3.39 | 87 |
| 6 | $CH_3O$ | $C_6H_4CH_3(p)$ | $C_{22}H_{28}ClNO_5$ 421.95 | 221–222 abs. ethanol | C: H: N: | 62.62 6.69 3.32 | 62.37 7.06 3.41 | 82 |
| 7 | $C_2H_5O$ | $C_6H_4CH_3(p)$ | $C_{24}H_{32}ClNO_5$ 449.95 | 187–189 EtOH ether | C: H: N: | 64.07 7.17 3.11 | 63.32 7.55 2.57 | 85 |
| 8 | $CH_3O$ | $C_6H_4Cl(p)$ | $C_{21}H_{25}Cl_2NO_5$ 442.34 | 220–223 methanol | C: H: N: | 57.02 5.70 3.17 | 56.80 5.93 3.25 | 95 |
| 9 | $C_2H_5O$ | $C_6H_4Cl(p)$ | $C_{23}H_{29}Cl_2NO_5$ 470.40 | 189–192 ethanol | C: H: N: | 58.73 6.21 2.98 | 58.79 5.99 2.95 | 90 |
| 10 | $C_2H_5O$ | $C_6H_4NO_2(p)$ | $C_{23}H_{29}ClN_2O_7$ 481.95 | 195–198 ethanol/ | C: H: | 57.32 6.06 | 57.13 6.38 | 85 |

TABLE 1-continued

1-[1'-(Hydroxymethyl)-1'-(O—acyl)-methyl]-6,7-dialkoxyl-1,2,3,4-tetrahydroisoquinoline hydrochlorides of formula (I/1)

| Example | $R^1 = R^2$ | $R^9$ | Formula/ Molecular weight | Melting point (°C.) Solvent | Analysis calculated | found | Yield (%) |
|---|---|---|---|---|---|---|---|
| 11 | $CH_3O$ | $C_6H_3(OCH_3)_2$ (m, p) | $C_{23}H_{30}ClNO_7$ 467.94 | 148–150 ether ethanol | N: 5.81<br>C: 59.03<br>H: 6.46 | 5.52<br>58.48<br>6.07 | 78 |
| 12 | $C_2H_5O$ | $C_6H_3(OCH_3)_2$ (m, p) | $C_{25}H_{34}ClNO_7$ 495.98 | 127–131 ethanol | N: 2.99<br>C: 60.54<br>H: 6.91 | 3.21<br>60.12<br>7.23 | 78 |
| 13 | $CH_3O$ | $C_6H_2(OCH_3)_3$ (m, p, m) | $C_{24}H_{32}ClNO_8$ 497.97 | 160–162 ethanol | N: 2.82<br>C: 57.88<br>H: 6.48 | 2.85<br>57.70<br>6.96 | 75 |
| 14 | $C_2H_5O$ | $C_6H_2(OCH_3)_3$ m, p, m) | $C_{26}H_{36}ClNO_8$ 526.03 | 155–162 ethanol | N: 2.81<br>C: 59.37<br>H: 6.90 | 3.17<br>59.53<br>7.21 | 78 |
| 15 | $CH_3O$ | $C_6H_3Cl_2$(m, p) | $C_{21}H_{24}Cl_3NO_5$ 476.78 | 173–176 ethanol | N: 2.66<br>C: 52.90<br>H: 5.07 | 2.86<br>52.05<br>5.39 | 79 |
| 16 | $C_2H_4O$ | $C_6H_3Cl_2$ (m, p) | $C_{23}H_{28}Cl_3NO_5$ 504.83 | 135–140 ethanol | N: 2.94<br>C: 54.72<br>H: 5.59<br>N: 2.77 | 2.90<br>54.52<br>5.52<br>2.57 | 89 |

EXAMPLE 17

Preparation of 1-[bis(chloromethyl)-methyl]-6,7-dimethoxy-1,2,3,4-tetrahydroisoquinoline hydrochloride 0.01 mole (3.0 g) of 1-[bis(hydroxymethyl)-methyl]-6,7-dimethoxy-1,2,3,4-tetrahydroisoquinoline hydrochloride is powdered and suspended in 6.5 ml of sulfinyl dichloride. The mixture is then slightly heated under stirring for 30 minutes. The excess of sulfinyl dichloride is distilled off under vacuum (ejector jet pump), the residue is taken up in benzene and evaporated to dryness. The obtained oily residue is crystallized from a mixture of ethanol and ether.

Melting point: 216° to 219° C. Yield: 76%. Analysis for $C_{14}H_{20}Cl_3NO_2$ (340.68): calculated: C 49.36%, H 5.92%; found: C 49.76%, H 6.12%.

The corresponding diethoxy analogue can be prepared from 1-[bis(hydroxymethyl)-methyl]-6,7-diethoxy-1,2,3,4-tetrahydroisoquinoline hydrochloride in an analogous manner.

Melting point: 149° to 153° C. (ethanol/ether). Yield: 73%. Analysis for $C_{16}H_{24}Cl_3NO_2$ (368.73): calculated: C 52.12%, H 6.56%; found: C 52.65%, H 6.37%.

EXAMPLE 18

Preparation of 1-[bis(bromomethyl)-methyl]-6,7-diethoxy-1,2,3,4-tetrahydroisoquinoline hydrobromide To a suspension of 0.01 mole (3.5 g) 1-[bis-(hydroxymethyl)-methyl]-6,7-diethoxy-1,2,3,4-tetrahydroisoquinoline in 30 ml of absolute benzene 0.03 mole (20 ml) of phosphorus tribromide is portionwise added, under ice cooling and stirring. The reaction mixture is refluxed for 45 minutes. After cooling 20 ml of cold water are added, and the mixture is refluxed for additional 10 minutes. After cooling, the two phases are separated, and the benzene phase is extracted with two 20-ml portions of water. The combined aqueous phases are washed with two 20-ml portions of diethyl ether. The aqueous phase is then adjusted to pH 8 with sodium hydroxide and extracted with four 30-ml portions of ether. The extract is dried and evaporated. A solution of hydrogen bromide in absolute ethanol is added to the residue to yield 1-[bis(bromomethy)-methyl]-6,7-diethoxy-1,2,3,4-tetrahydroisoquinoline hydrobromide in a crystalline form.

Melting point: 188° to 190° C. (ethanol/ether). Yield: 78%. Analysis for $C_{16}H_{24}Br_3NO_2$ (502.09): calculated: C 38.27%, H 4.82%, N 2.79%; found: C 38.26%, H 4.92%, N 2.87%.

EXAMPLE 19

Preparation of 1-[bis(bromomethyl)-methyl]-6,7-diethoxy-1,2,3,4-tetrahydroisoquinoline hydrobromide To 0.01 mole (2.7 g) of 1-[bis(hydroxymethyl)-methyl]-6,7-diethoxy-1,2,3,4-tetrahydroisoquinoline 100 ml of absolute tetrachloromethane are added, and the solution is saturated with hydrogen bromide gas under ice cooling. The solvent is evaporated under reduced pressure to yield the hydrobromide of the starting substance as a viscous mass. To this residue 0.03 mole (20 ml) of phosphorus tribromide is added, and the mixture is heated on a water bath for 4 hours. After cooling, the aimed compound is separated from the reaction mixture as a crystalline substance. The compound is filtered off and thoroughly washed with absolute ether or absolute acetone. The physical and spectroscopical data of the compound obtained are identical with those of the compound prepared according to Example 18.

EXAMPLE 20

Preparation of 1-[1'-(chloromethyl)-1''-(benzoyloxymethyl)-methyl]-6,7-dimethoxy-1,2,3,4-tetrahydroisoquinoline hydrochloride Starting from 1-[1'-(hydroxymethyl)-1''-(benzoyloxymethyl)-methyl]-6,7-dimethoxy-1,2,3,4-tetrahydroisoquinoline prepared according to Example 2, otherwise following the procedure described in Example 1, Step (B), the aimed compound is obtained with a melting point (after crystallization from 96% ethanol) of 196° to 198° C.

Analysis for $C_{21}H_{25}Cl_2NO_2$ (426.25): calculated: C 59.14%, H 5.91%, N 3.25%, Cl 16.63%; found: C 60.54%, H 6.20%, N 3.44%, Cl 16.58%.

EXAMPLE 21

Preparation of
1-[1'-(chloromethyl)-1''-(hydroxymethyl)-methyl]-6,7-dimethoxy-1,2,3,4-tetrahydroisoquinoline hydrochloride 0.01 mole (4.26 g) of 1-[1'-(chloromethyl)-1''-(benzoyloxymethyl)-methyl]-6,7-dimethoxy-1,2,3,4-tetrahydroisoquinoline hydrochloride prepared according to Example 20 is boiled in a mixture of 50 ml of a 10% aqueous hydrogen chloride solution and 10 ml of ethanol for 2.5 hours. After evaporation the aimed compound is obtained in a crystalline form.

Melting point (after recrystallization from 96% ethanol): 216°–219° C. Yield: 67%. Analysis for $C_{14}H_{21}Cl_2NO_3$ (322.23): calculated: C 52.18%, H 6.56%, N 4.34%, Cl 22.00%; found: C 52.68%, H 6.56%, N 4.48%, Cl 21.86%.

EXAMPLE 22

Preparation of
1-[bis(phenylcarbamoyloxymethyl)-methyl]-2-benzyl-6,7-dimethoxy-1,2,3,4-tetrahydroisoquinoline (A) 1-[bis(Hydroxymethyl)-methyl]-2-benzyl-6,7-dimethoxy-1,2,3,4-tetrahydroisoquinoline hydrochloride 0.01 mole (3.7 g) of the N-benzoyl compound prepared according to Example 1, Step A is reacted with 3 g of lithium tetrahydroaluminate (III) in absolute tetrahydrofuran. The reaction mixture is refluxed for 3 hours, worked up in a usual manner, and is then coverted into the aimed hydrochloride salt Melting point: 177° to 179° C. (ethanol/ether). Yield: 69%. Analysis for $C_{21}H_{28}ClNO_4$ (393.90): calculated: C 64.03%, H 7.16%, N 3.56%; found: C 63.65%, H 7.53%, N 3.12%.

(B) 0.01 mole of the compound obtained in Step (A) is boiled with 0.02 mole of phenyl isocyanate for 4 to 6 hours. Evaporation of the reaction mixture yields the aimed compound in a crystalline form.

Melting point: 185° C. (toluene). Analysis for $C_{35}H_{37}N_3O_6$ (595.70): calculated: C 70.57%, H 6.26%, N 7.05%; found: C 70.09%, H 6.33%, N 6.54%.

The compounds of formula (I/2) set forth in Table 2 can be prepared in an analogous manner, by proper selection of the starting substances.

EXAMPLE 27

Preparation of
1-[bis(phenylcarbamoyloxymethyl)-methyl]-2-(phenylcarbamoyl)-6,7-dimethoxy-1,2,3,4-tetrahydroisoquinoline 0.01 mole of 1-[bis(hydroxymethyl)-methyl]-6,7-dimethoxy-1,2,3,4-tetrahydroisoquinoline is reacted with 0.03 mole of phenylisocyanate in toluene, as described in Example 22. The aimed compound is obtained, which has the same physical and analytical characteristics as the product of Example 26 (Table 2).

EXAMPLE 28

Preparation of
1-[1'-(hydroxymethyl)-1''-(benzoyloxymethyl)-methyl]-2-benzoyl-6,7-dimethoxy-1,2,3,4-tetrahydroisoquinoline 0.01 mole (4.08 g) of 1-[1'-(hydroxymethyl)-1''-(benzoyloxymethyl)-methyl]-6,7-dimethoxy-1,2,3,4-tetrahydroisoquinoline hydrochloride is suspended in 50 ml of benzene, and to the suspension 25 ml of a 2M aqueous sodium hydroxide solution are added. 0.011 mole of benzoyl chloride is added with stirring to the reaction mixture and the mixture is stirred at room temperature for one hour. The organic phase is separated and the aqueous phase is extracted with two 50-ml portions of benzene. Drying and evaporation of the combined organic phases yields the aimed compound in a crystalline form.

Melting point: 135° to 138° C. (benzene). Yield: 85%. Analysis for $C_{28}H_{29}NO_6$ (475.56): calculated: C 70.72%, H 6.15%, N 2.95%; found: C 71.05% H 5.92%, N 3.01%.

EXAMPLE 29

Preparation of
1-[1'-(hydroxymethyl)-1''-(benzoyloxymethyl)-methyl]-2-(N'-phenyl-thiocarboxamido)-6,7-dimethoxy-1,2,3,4-tetrahydroisoquinoline 5 mmoles (2.04 g) of 1-[1'-(hydroxymethyl)-1''-(benzoyloxymethyl)-methyl]-6,7-dimethoxy-1,2,3,4-tetrahydroisoquinoline hydrochloride are dissolved in 20 ml of water, to the solution 5 ml of a 10% aqueous sodium hydroxide solution are added and it is then extracted with three 20-ml portions of benzene. The combined benzene phases ae dried, whereupon 5 mmoles of phenyl isothiocyanate are added. After 24 hours the precipitated product is filtered off and crystallized from ethanol to yield the aimed compound.

Melting point: 155° to 158° C. Yield: 79%. Analysis for $C_{28}H_{30}N_2O_5S$ (506.61): calculated: C 66.38%, H 5.97%, N 5.53%; found: C 66.58%, H 6.35%, N 5.16%.

We claim:

1. Bis(substituted methyl)methylisoquinoline derivatives of the formula (I),

TABLE 2

Compounds of formula (I/2)

| Example | $R^1 = R^2$ | $R^3$ | $R^9$ | Formula Molecular weight | Melting point (°C.) Solvent | Analysis Calculated found C | H | N |
|---|---|---|---|---|---|---|---|---|
| 23 | CH$_3$O | COC$_3$H$_5$ | NHC$_4$H$_9$ | C$_{31}$H$_{43}$N$_3$O$_7$ 569.70 | 87 benzene: | 65.36 65.30 | 7.61 7.77 | 7.37 6.98 |
| 24 | CH$_3$O | COC$_6$H$_5$ | NHC$_6$H$_5$ | C$_{35}$H$_{35}$N$_3$O$_2$ 609.68 | 182–184 benzene | 68.95 69.81 | 5.79 6.17 | 6.89 6.97 |
| 25 | CH$_3$O | COCH$_3$ | NHC$_6$H$_5$ | C$_{30}$H$_{33}$N$_3$O$_7$ 547.61 | 164–165 benzene | 65.80 65.44 | 6.07 7.07 | 7.67 8.28 |
| 26 | CH$_3$O | CONHC$_6$H$_5$ | NHC$_6$H$_5$ | C$_{35}$H$_{36}$N$_4$O$_7$ 624.70 | 173–174 benzene | 67.29 69.48 | 5.81 5.79 | 8.97 9.25 |

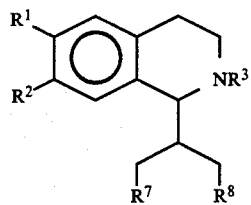 (I)

wherein
$R^1$ and $R^2$ represent hydroxyl or alkoxy having from 1 to 6 carbon atoms,
$R^3$ is hydrogen, phenyl $C_1$–$C_4$-alkyl; or a

group,
in which
$R^4$ is alkyl having from 1 to 5 carbon atoms, unsubstituted phenyl, phenyl substituted by halogen, alkyl having from 1 to 4 carbon atoms, alkoxy having from 1 to 4 carbon atoms or nitro or —NH-phenyl,
X is oxygen or sulfur,
$R^7$ is hydroxyl, halogen or an

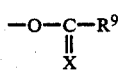

group,
$R^8$ is halogen, alkoxy having from 1 to 4 carbon atoms or an

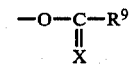

group, in which X has the same meaning as defined above, and
$R^9$ independently from $R^4$ may have the same meanings as defined for $R^4$, or is an —NH($C_{1-4}$-alkyl) or $C_{3-6}$-cyclogroup,
and physiologically acceptable salts thereof.

2. A compound of the formula (I) as defined in claim 1, wherein X is oxygen.

3. A compound of the formula (I) as defined in claim 1, wherein $R^7$ is hydroxyl and $R^8$ is an

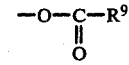

group.

4. The compound of the formula (I) as defined in claim 1 which is 1-[1'-(hydroxymethyl)-1'-(benzoyloxymethyl)-methyl]-6,7-dimethoxy-1,2,3,4-tetrahydroixoquinoline hydrochloride.

5. The compound of the formula (I) as defined in claim 1 which is 1-[1'-(hydroxymethyl)-1'-(m,p,m'-trimethoxybenzoyloxymethyl)-methyl]-6,7-diethoxy-1,2,3,4-tetrahydroisoquinoline hydrochloride.

6. A pharmaceutical composition having immunsuppressive, anti-depressive, analgesic, anti-pyretic, antihypoxial, and gastric acid inhibiting activity comprising as active ingredient an effective amount of at least one compound of formula (I) as defined in claim 1 or physiologically acceptable salts thereof, in association with pharmaceutical carriers and/or excipients.

* * * * *

UNITED STATES PATENT AND TRADEMARK OFFICE
CERTIFICATE OF CORRECTION

PATENT NO. : 4,654,351
DATED : March 31, 1987
INVENTOR(S) : Gabor BERNATH et al.

It is certified that error appears in the above-identified patent and that said Letters Patent is hereby corrected as shown below:

[cyclogroup] should be:

cycloalky group

Column 14, line 10

Signed and Sealed this

Twenty-ninth Day of September, 1987

Attest:

DONALD J. QUIGG

*Attesting Officer*  *Commissioner of Patents and Trademarks*